United States Patent [19]

Abraham

[11] Patent Number: 4,874,236
[45] Date of Patent: Oct. 17, 1989

[54] OPHTHALMOLOGIC APPARATUS FOR FUNDUS EXAMINATION

[75] Inventor: Fabian Abraham, Bnei-Brak, Israel

[73] Assignee: Ramot University Authority for Applied Research and Industrial Development Ltd., Tel-Aviv, Israel

[21] Appl. No.: 163,049

[22] Filed: Mar. 2, 1988

[30] Foreign Application Priority Data

Mar. 4, 1987 [IL] Israel .......................................... 81776

[51] Int. Cl.$^4$ ................................................ A61B 3/10
[52] U.S. Cl. ....................................... 351/205; 351/214
[58] Field of Search ................ 351/205, 214, 216, 217, 351/221

[56] References Cited

U.S. PATENT DOCUMENTS

| | | | |
|---|---|---|---|
| 2,999,422 | 9/1961 | Papritz | 351/214 |
| 3,944,343 | 3/1976 | Mueller | 351/214 |

Primary Examiner—Rodney B. Bovernick
Attorney, Agent, or Firm—Benjamin J. Barish

[57] ABSTRACT

Ophthalmologic apparatus for fundus examination of a patient's eyes, comprises a base, an illumination device carried by the base and rotatable about a vertical axis, a microscope carried by the base and rotatable about the vertical axis, a fixture for fixing the patient's head and eyes with respect to the vertical axis, a vertical rod carried by the base along the vertical axis, and a lens carried at the upper end of the vertical rod in the optical axis of the microscope and the examined eye and displaced from the vertical axis towards the examined eye such as to image the retina of the examined eye at a location for reimaging it by the microscope. The described apparatus enables funduscopic examinations to be made in a very convenient manner using existing opthalmological slit lamps.

14 Claims, 2 Drawing Sheets

OPHTHALMOLOGIC APPARATUS FOR FUNDUS EXAMINATION

BACKGROUND OF THE INVENTION

The present invention relates to ophthalmologic apparatus for fundus examination of a patient's eyes. The invention also relates to an attachment to a slit lamp to adapt it for use in such examination.

A modern opthalmological slit lamp is a versatile instrument for comfortable eye anterior segment examination under high magnification and stereoscopic observation. For fundus examination, an accessory lens is necessary to image the retina in a position where it can be reimaged by the microscope. A contact lens, as well as high power negative or positive noncontact lenses, can be used for this purpose. A double aspheric +90 diopter noncontact lens with anti-reflective coating has been found particularly useful since it provides a high quality, magnified, real, inverted, stereoscopic retinal image. Further, it avoids the difficulties caused by contact lens examination in apprehensive patients, children, or following eye surgery. It also avoids the small size retinal field provided by the negative noncontact lens. However, this slit lamp funduscope is not yet widely used, since the need to align the hand-held or mounted +90 diopter lens in front of the examined eye, and simultaneously to manipulate the microscope with the other hand, makes the technique cumbersome and unattractive for routine funduscopy.

BRIEF SUMMARY OF THE INVENTION

An object of the present invention is to provide ophthalmologic apparatus including an attachment to the existing slit lamp, avoiding the above difficulties, and the facilitating the use of such slit lamp for routine funduscopy.

According to the present invention, there is provided opthalmologic apparatus for fundus examination of a patient's eyes, comprising: a base, an illumination device carried by the base and rotatable about a vertical axis, a microscope carried by said base and rotatable about said vertical axis, a fixture for fixing the patient's head and eyes with respect to said vertical axis, a vertical rod carried by said base along said vertical axis, and a lens carried at the upper end of the vertical rod in the optical axis of the microscope and the examined eye and displaced from said vertical axis towards the examined eye for a fixed distance, corresponding to the power of said lens, such as to image the retina of the examined eye at a location for reimaging it by the microscope.

In the described preferred embodiment, the lens is a double aspheric +90 diopter lens, and is carried by a horizontal support attached to the upper end of the vertical rod 11 mm from the mentioned vertical axis towards the location of the examined eye.

According to further features in the described preferred embodiment, the lens is mounted on the horizontal support for lateral movement about 6 mm on each side of the optical axis; in addition, the lens is mounted for limited vertical movement along the vertical axis about 6 mm below the optical axis and as much as desired above the optical axis.

The invention also provides an attachment having the above features for use with existing ophthalmological slit lamps.

As will be described more particularly below, the described apparatus and attachment enable funduscopic examinations to be made in a very convenient manner using existing opthalmological slit lamps.

BRIEF DESCRIPTION OF THE DRAWINGS

The invention is herein described, by way of example only, with reference to the accompanying drawings, wherein.

DESCRIPTION OF A PREFERRED EMBODIMENT

Figure 1:
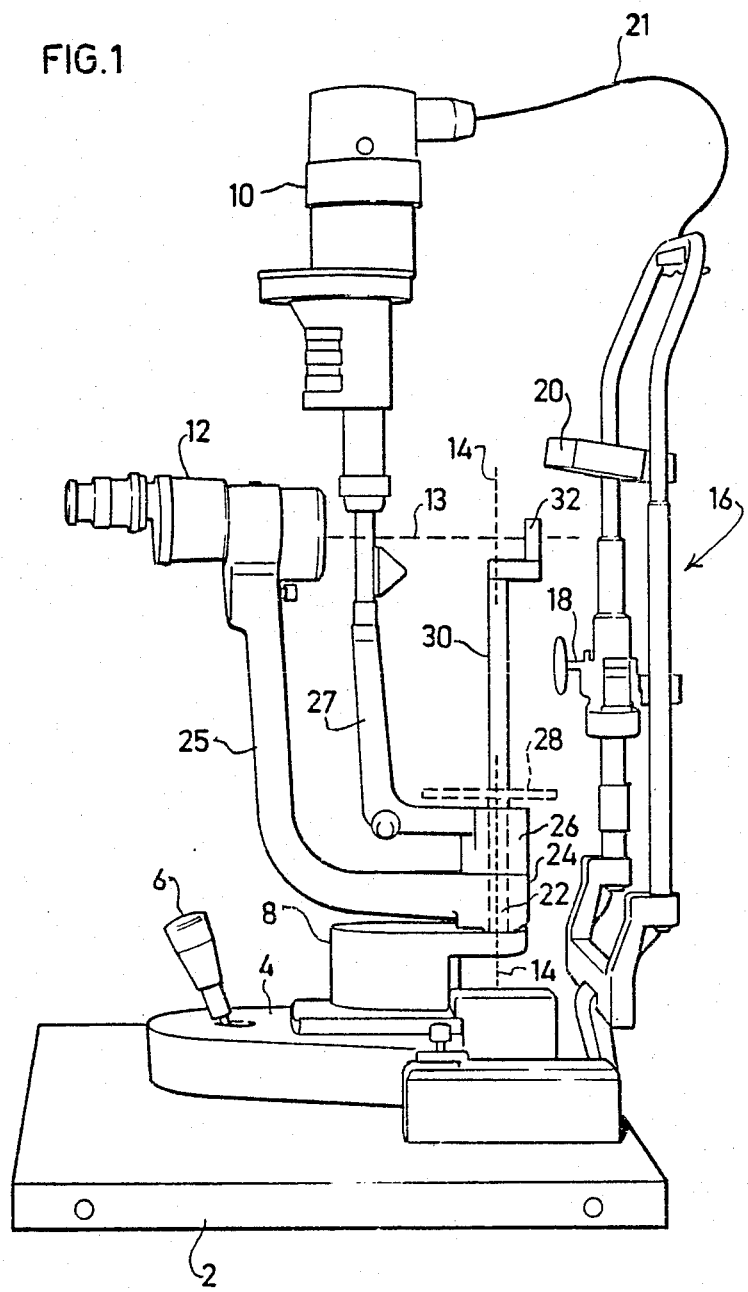
FIG. 1 illustrates one form of opthalmologic apparatus constructed in accordance with the present invention.
Figure 2:
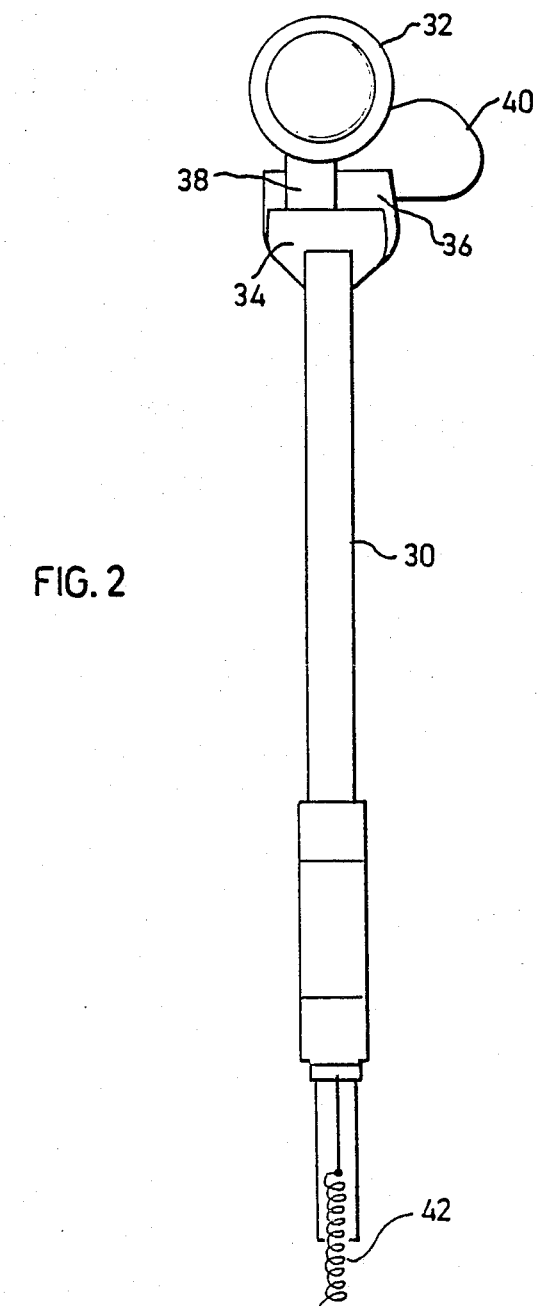
FIG. 2 illustrates only the attachment used in the opthalmologic apparatus of FIG. 1.

The apparatus illustrated in FIG. 1 is basically a standard slit lamp but includes the novel attachment illustrated in FIG. 2 to adapt the apparatus for funduscopic examination. Thus, the apparatus includes a base 2 supporting a carriage 4 movable along both axes in the horizontal plane by manipulating handle 6. Carriage 4 supports a mounting 8 which mounts an illumination device 10 and a microscope 12, both of which are rotatable about the same vertical axis 14. Base 2 further supports a fixture, generally designated 16, which includes a chin rest 18 and a forehead rest 20 for the patient, to fix the patient's head so as to align the examined eye with the optical axis 13 of the microscope 12. Fixture 16 further supports a cable 21 for supplying electricity to illumination device 10.

Such apparatus is well known and various types are commercially available, and therefore further features of its construction and operation are not set forth herein.

In the conventional apparatus, the vertical axis 14, which is common to the illumination device 10 and the microscope 12, is defined by a tubular member 22 fixed to mounting 8 which rotatably receives sleeve 24 of the supporting arm of microscope 12, and sleeve 26 of the supporting arm 27 of the illumination device 10. Tubular member 22 is also adapted to receive guide plate 28 for a tonometer (not shown) to measure eye pressure. To adapt this apparatus for use with the present invention, the tonometer guide plate 28 is removed, and tubular member 22 is used for receiving the novel attachment, as particularly illustrated in FIG. 2.

The attachment illustrated in FIG. 2 comprises a vertical rod 30 carrying a lens 32 at its upper end. Rod 30 is of such length that when inserted within tubular member 22, lens 32 will be in the optical axis 13 between the microscope 12 and the examined eye of the patient as fixed by the chin rest 18 and forehead rest 20. Lens 32 images the retina of the examined eye in a position for reimaging it by the microscope. Lens 32 is preferably a double aspheric +90 diopter lens of 18 mm diameter with an anti-reflective coating.

As shown in FIG. 2, rod 30 further includes a supporting member 34 attached to the upper end of the vertical rod 30 and extending along the optical axis 13 towards the position of the examined eye a distance of 11 mm.

In addition, lens 32 is mounted on support 34 so as to be moveable laterally with respect to the optical axis. For this purpose, support 34 includes a horizontal guide bar 36 extending in the lateral transverse direction with respect to the optical axis 13, and the lens 32 carries a pair of arms 38 slidably received on guide bar 36 for movement up to 6 mm on each side of the optical axis. A handle 40 attached to the holder for lens 32 facilitates the lateral movement of the lens with respect to the guide bar 36.

Lens 32 is also movable vertically with respect to the optical axis 13 between the microscope 12 and the examined eye as fixed by the chin rest 18 and forehead rest 20. For this purpose, the lower end of the vertical rod 30 carries a coiled spring 42. One end of the coiled spring is fixed within rod 30, and the opposite end projects from the rod a predetermined distance so that when the rod 30 is inserted within the bore in channel member 22, spring 42 will locate lens 32 at the optical axis 13. However, the operator may slightly press down or elevate the rod to also provide vertical movement of the lens with respect to the optical axis. This downward movement is limited to 6 mm; the upward movement is unlimited.

The above-described horizontal and vertical movements of the lens with respect to the optical axis 13 between the microscope and the examined eye, provide a number of advantages, as will be described more particularly below.

The illustrated apparatus may be used in the following manner:

The apparatus illustrated in FIG. 1, but without the attachment including vertical rod 30 and lens 32, may be used in the conventional manner for eye anterior segment examination. When such examination has been completed, and while the patient with the pupil dilated is still fixed in position by the fixture chin rest 18 and forehead rest 20, the tonometer guiding plate 28 is removed, and the vertical rod 30 carrying the lens 32 is inserted in tubular member 22 along axis 14. As described earlier, axis 14 is the common vertical axis about which the illumination device 10 and the microscope 12 may both be rotated. Accordingly, the +90 diopter lens 32 carried at the upper end of the vertical rod 30 is automatically located exactly in the optical axis 13 between the microscope and the examined eye, and 11 mm from the vertical axis 14, to image the retina for reimaging in the microscope, thereby obviating the need for further adjustment.

The microscope 12, with the narrow slit beam produced by illumination device 10 in mid-position, is then pulled toward the examiner to its maximum position until the eye anterior segment becomes visible. The microscope is then moved towards the patient's eye, whereupon a clear stereoscopic retinal image with an illuminated slit appears in lens 32. This happens when the lens is in its mid-horizontal position and reaches about 1 cm to the cornea.

About 40° of the eye posterior pole can be examined stereoscopically under excellent slit illumination. A slight horizontal lateral sliding of lens 32, in conjunction with a small displacement of the microscope in the opposite direction, extends horizontally the visible retinal area. Likewise, displacing the lens vertically by the spring 42, carried at the lower end of vertical rod 30, increases the retinal view vertically. If desired, more peripheral retina can be seen by having the patient move his eye in a certain direction, or follow a guiding target.

By using 10× magnification on the microscope, good retinal images can be seen and photographed from eyes with up to 20 diopter refractive ametropia. Annoying light reflexes can be avoided by slightly sliding the slit beam, or by gently rotating the supporting rod or the light source. In addition, the microscope may be moved slightly, without moving the lens, whenever it is desired to see a band of the retina by retro-illumination. Further, if a different power lens 32 is desired, this may be easily substituted, in which case the fixed distance (11 mm between the lens and the vertical axis of rod 30 for a +90 diopter lens), would be appropriately changed.

After the funduscopic examination has been completed, the vertical rod 30 with lens 32 may be removed, and the slit lamp is again ready for anterior segment examination.

The illustrated apparatus is simple to use, thereby substantially eliminating the need for further training. Moreover, it enables the examiner to perform both anterior and posterior segment eye examinations under good conditions and at the same time by using the same slit lamp.

While the invention has been described with respect to one preferred embodiment applied to one type of slit lamp, it will be appreciated that the invention can be used with many other types of slit lamps, and that many variations, modifications and other applications of the invention may be made.

What is claimed is:

1. Ophthalmologic apparatus for fundus examination of a patient's eyes, comprising: a base, an illumination device carried by said base and rotatable about a vertical axis, a microscope carried by said base and rotatable about said vertical axis, a fixture for fixing the patient's head and eyes with respect to said vertical axis, a vertical rod carried by said base along said vertical axis, and a lens carried at the upper end of said vertical rod in the optical axis of the microscope and the examined eye and displaced from said vertical axis towards said examined eye for a fixed distance, corresponding to the power of said lens, such as to image the retina of the examined eye at a location for reimaging it by the microscope.

2. The apparatus according to claim 1, wherein said lens is a double aspheric +90 diiopter lens and is carried by a horizontal support attached to the upper end of said vertical rod and is positioned by said horizontal support about 11 mm along said optical axis towards the location of the examined eye.

3. The apparatus according to claim 1, wherein said lens is mounted for lateral movement with respect to said optical axis.

4. The apparatus according to claim 3, wherein said lens includes a handle to facilitate sliding it laterally.

5. The apparatus according to claim 1, wherein said lens is also mounted for vertical movement along said vertical axis.

6. The apparatus according to claim 5, wherein said vertical rod includes a spring permitting limited vertical movement thereof and of the lens carried thereby.

7. The apparatus according to claim 1, wherein said vertical rod, together with the lens carried thereby, is removably mounted in a tubular member carried by said base along said vertical axis.

8. An attachment for an ophthalmologic apparatus for fundus examination of a patient's eye comprising a base, a slit lamp carried by said base and rotatable about a vertical axis, a microscope carried by said base and rotatable about said vertical axis, and a fixture for fixing the patient's head and eyes to be examined with respect to said vertical axis; said attachment comprising a vertical rod to be attached to said base and to extend along said vertical axis; and a lens carried at the upper end of said vertical rod so as to be positioned in the optical axis of the microscope and examined eye and displaced from said vertical axis towards said examined eye for a fixed distance, corresponding to the power of said lens, such as to image the retina of the examined eye in a position for reimaging it by the microscope.

9. The attachment according to claim 8, wherein said lens is a double aspheric +90 diopter lens and is carried by a horizontal support attached to the upper end of said vertical rod and is positioned by said horizontal support about 11 mm along said optical axis towards the location of the examined eye.

10. The attachment according to claim 8, wherein said lens is mounted for lateral movement with respect to said optical axis.

11. The attachment according to claim 8, wherein said lens includes a handle to facilitate sliding it laterally.

12. The attachment according to claim 8, wherein said lens is mounted for vertical movement along said vertical axis.

13. The attachment according to claim 8, wherein said vertical rod includes a spring permitting limited vertical movement thereof and of the lens carried thereby.

14. The attachment according to claim 8, wherein said vertical rod, together with the lens carried thereby, is removably mounted in a tubular member carried by said base along said vertical axis.

* * * * *